United States Patent
Kim

(10) Patent No.: US 8,052,596 B2
(45) Date of Patent: Nov. 8, 2011

(54) ARC-SHAPED FLEXIBLE PRINTED CIRCUIT FILM TYPE ENDOSCOPE USING IMAGING DEVICE

(75) Inventor: Gyung-Sub Kim, Suwon-si (KR)

(73) Assignee: Korea Plant Service & Engineering Co., Ltd., Gyeonggi-Do (KR)

( * ) Notice: Subject to any disclaimer, the term of this patent is extended or adjusted under 35 U.S.C. 154(b) by 588 days.

(21) Appl. No.: 12/274,978

(22) Filed: Nov. 20, 2008

(65) Prior Publication Data

US 2010/0041946 A1 Feb. 18, 2010

(30) Foreign Application Priority Data

Aug. 14, 2008 (KR) .................. 10-2008-0079894

(51) Int. Cl.
*A61B 1/04* (2006.01)
(52) U.S. Cl. ........ 600/129; 600/110; 600/128; 600/130; 600/140; 600/179; 348/82
(58) Field of Classification Search ............. 600/109, 600/110, 128–130, 139, 140, 179; 348/82–85
See application file for complete search history.

(56) References Cited

U.S. PATENT DOCUMENTS

| | | | | |
|---|---|---|---|---|
| 6,142,930 A * | 11/2000 | Ito et al. | .................. | 600/109 |
| 6,293,910 B1 * | 9/2001 | Yamakita et al. | .............. | 600/132 |
| 7,300,397 B2 * | 11/2007 | Adler et al. | .................... | 600/110 |
| 2002/0028982 A1 * | 3/2002 | Takahashi | ...................... | 600/110 |
| 2004/0176661 A1 * | 9/2004 | Futatsugi | ...................... | 600/110 |

FOREIGN PATENT DOCUMENTS

| | | | | |
|---|---|---|---|---|
| DE | 102004023866 B3 | * | 2/2006 | |
| EP | 2140802 A1 | * | 1/2010 | |
| JP | 05261065 A | * | 10/1993 | |
| JP | 08271809 A | * | 10/1996 | |
| JP | 11295517 | * | 10/1999 | |
| JP | 2003169773 | * | 6/2006 | |
| JP | 2006-319401 A | | 11/2006 | |
| JP | 2007244530 A | * | 9/2007 | |

* cited by examiner

*Primary Examiner* — Matthew Daniels
*Assistant Examiner* — Yana Belyaev
(74) *Attorney, Agent, or Firm* — Birch, Stewart, Kolasch & Birch, LLP

(57) ABSTRACT

Disclosed herein is an arc-shaped flexible printed circuit film type endoscope using an imaging device. The endoscope includes an image photographing means and an object insertion means. The image photographing means includes a head housing to which an imaging device and an illumination means are mounted, and functions to photograph an image. The object insertion means includes an arc-shaped flexible thin foil, an insulating adhesive film, a circuit film and an insulating protective film which are layered and inserted into an interior of an object to be inspected. The object insertion means is connected at one end thereof to the image photographing means and connected at the other end to a transmission cable via a connector.

6 Claims, 3 Drawing Sheets

ARC-SHAPED FLEXIBLE PRINTED CIRCUIT FILM TYPE ENDOSCOPE USING IMAGING DEVICE

BACKGROUND OF THE INVENTION

1. Field of the Invention

The present invention relates generally to an industrial endoscope and, more particularly, to an arc-shaped flexible printed circuit film type endoscope using an imaging device in which a flexible printed circuit film is connected to a head housing accommodating a charge coupled device (CCD) camera or a complementary metal-oxide-semiconductor (CMOS) sensor as the imaging device so that the endoscope can be mounted to a small space such as a robot to easily inspect the interior of a narrow heat transfer tube, and the endoscope has a small bending radius to be conveniently handled in the small space.

2. Description of the Related Art

Generally, a plurality of heat transfer tubes is mounted on a secondary side's tube sheet of a steam generator installed in a nuclear power plant, with very narrow gaps formed between the heat transfer tubes. Here, sludge or impurities may enter the gaps between the heat transfer tubes, thus causing damage to the heat transfer tubes.

Therefore, in order to prevent the heat transfer tubes from being damaged by the sludge or impurities, visual inspection is periodically conducted. The visual inspection is performed through endoscopy using an endoscope camera which is mounted to a micro robot or the like.

Endoscopy is the non-destructive inspection method of visually inspecting the interior of a human body organ or an object without impairing the human body organ or the object, by inserting an insertion tube into the human body organ or the object.

Endoscopes are typically classified into medical and industrial endoscopes according to the object to be inspected. Among them, the manufacture of the industrial endoscope is difficult because its insertion part is small and thin.

Thus, in Korea, the industrial endoscope has not been researched and developed nor has it come onto the market yet. The supply of most endoscopes depends on imports.

The industrial endoscope includes an input-output unit for visually inspecting an object, a light source, and an insertion tube. Since most inspection instruments are too large to be inspected by an inspector, a lot of time, labor and expenses are required.

Further, the industrial endoscope adopts an analogue method. Thus, in order to store photographed images, photographs must be printed through chemical treatment, and the inspected result must be read via image equipment which is installed in an inspection site, so that there are restrictions of time and space. Further, since it is impossible to transmit data of the inspected result over a network, it is impossible share the data in real time.

In consideration of these aspects, as the conventional industrial endoscope which has been used to visually inspect the heat transfer tubes, an endoscope which has an industrial endoscope camera (including an endoscope camera and a CCD sensor) and a belt or a chain having a cable therein has been proposed.

The conventional endoscope is problematic in that the chain or belt is thick, so that it occupies a large space when rolled into a circular shape, and therefore it is difficult to mount the endoscope to a small space such as a robot so as to inspect the interior of a narrow heat transfer tube.

Further, the conventional belt- or circular cable-type endoscope camera is problematic in that when it is constructed to be very thin, it is too flexible, so that it is difficult to maintain strength of linear extension.

However, the endoscope according to the present invention uses an arc-shaped flexible thin foil, so that linearity is ensured in shape even though the endoscope comprises a very thin film, thus the endoscope has both linearity and flexibility.

Further, the endoscope camera, the cable, an illumination part and other parts are integrally installed in the chain- or belt-type feeding means, so that a bending radius is large. Thus, it is difficult to mount the conventional endoscope to a narrow space such as a robot and to handle it.

Meanwhile, in order to photograph a small space, there has been proposed Japanese Patent Laid-Open Publication No. 2006-319401, which is entitled "Remote Inspection System".

The remote inspection system includes a CMOS image sensor as an imaging device of a video camera. By manipulating a power supply for a video camera and white LED which is connected in a conduction state through a flexible spiral metal tube to an inspection head having the white LED for illumination, the remote inspection system photographs a narrow space.

Thus, a photographing unit includes the CMOS sensor and the illumination part, so that it is possible to photograph and inspect a small space. However, since a circuit means or a transmission means for processing or transmitting a photographed image cannot be formed on the spiral metal tube itself, the circuit means or the transmission means for processing or transmitting the photographed image must be provided separately from the spiral metal tube, thus inconveniencing a manufacturer.

SUMMARY OF THE INVENTION

Accordingly, the present invention has been made keeping in mind the above problems occurring in the prior art, and an object of the present invention is to provide an arc-shaped flexible printed circuit film type endoscope using an imaging device, in which a flexible printed circuit film is connected to a head housing accommodating a charge coupled device (CCD) camera or a complementary metal-oxide-semiconductor (CMOS) sensor as the imaging device, so that the endoscope can be mounted to a small space such as a robot to easily inspect the interior of a narrow heat transfer tube or gaps between heat transfer tubes.

Another object of the present invention is to provide an arc-shaped flexible printed circuit film type endoscope using an imaging device, which utilizes a flexible printed circuit film to have a small bending radius, thus being convenient to manipulate the endoscope in a small space.

A further object of the present invention is to provide an arc-shaped flexible printed circuit film type endoscope using an imaging device, which utilizes a flexible thin foil having an arc-shaped cross-section, thus ensuring linearity in shape even though the endoscope is very thin, therefore having both linearity and flexibility.

Yet another object of the present invention is to provide an arc-shaped flexible printed circuit film type endoscope using an imaging device, which utilizes a flexible printed circuit film so that a circuit means or a transmission means for processing or transmitting an image photographed by the imaging device are formed on the flexible printed circuit film, thus realizing a simple structure, therefore achieving high economic efficiency due to reduction in time and costs required to manufacture a product, and increasing the reliability of endoscopy because there is no possibility of failure or malfunction, and increasing the life-span of the endoscope such that it can be reliably used for a lengthy period of time.

In order to accomplish the above objects, the present invention provides an arc-shaped flexible printed circuit film type endoscope using an imaging device, which includes an image photographing means and an object insertion means. The image photographing means includes a head housing to which an imaging device and an illumination means are mounted, and functions to photograph an image. The object insertion means includes an arc-shaped flexible thin foil, an insulating adhesive film, a circuit film and an insulating protective film which are layered and inserted into an interior of an object to be inspected. The object insertion means is connected at one end thereof to the image photographing means and connected at the other end to a transmission cable via a connector.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, an arc-shaped flexible printed circuit film type endoscope using an imaging device according to the preferred embodiment of the present invention will be described in detail with reference to the accompanying drawings.

Figure 1:
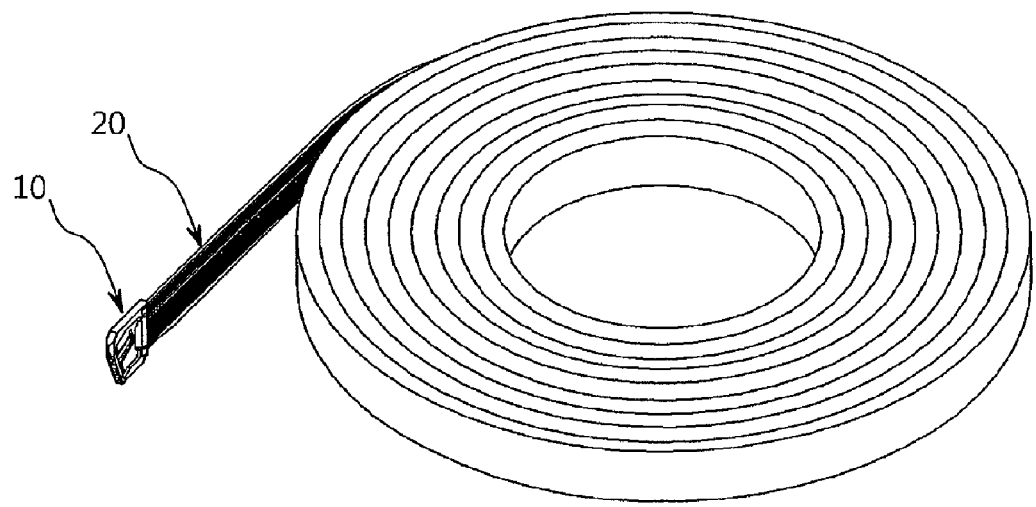
FIG. 1 is a perspective view illustrating an arc-shaped flexible printed circuit film type endoscope using an imaging device according to the present invention.
Figure 2:
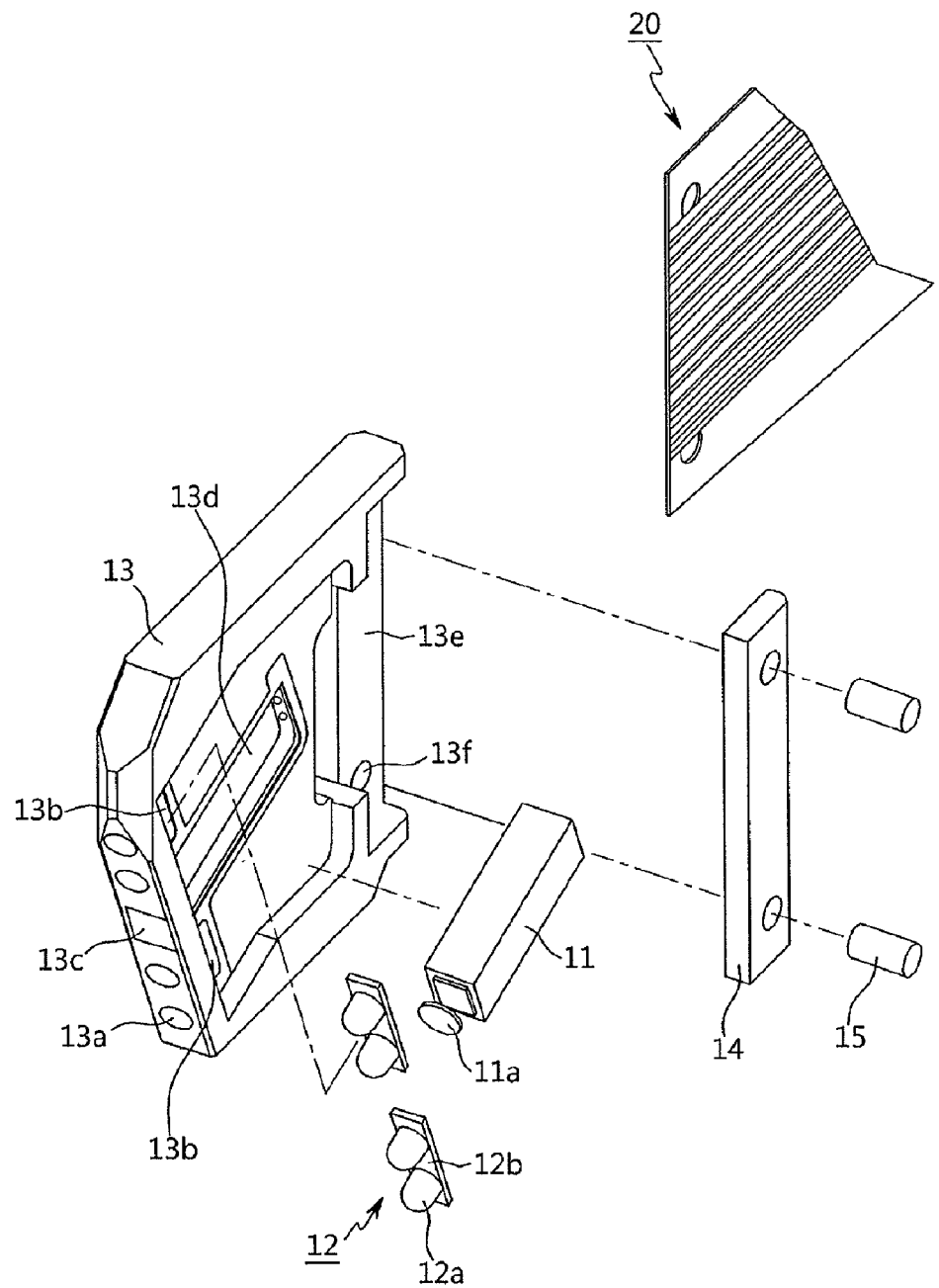
FIG. 2 is an exploded perspective view depicting the important parts of the arc-shaped flexible printed circuit film type endoscope using the imaging device according to the present invention.
Figure 3:
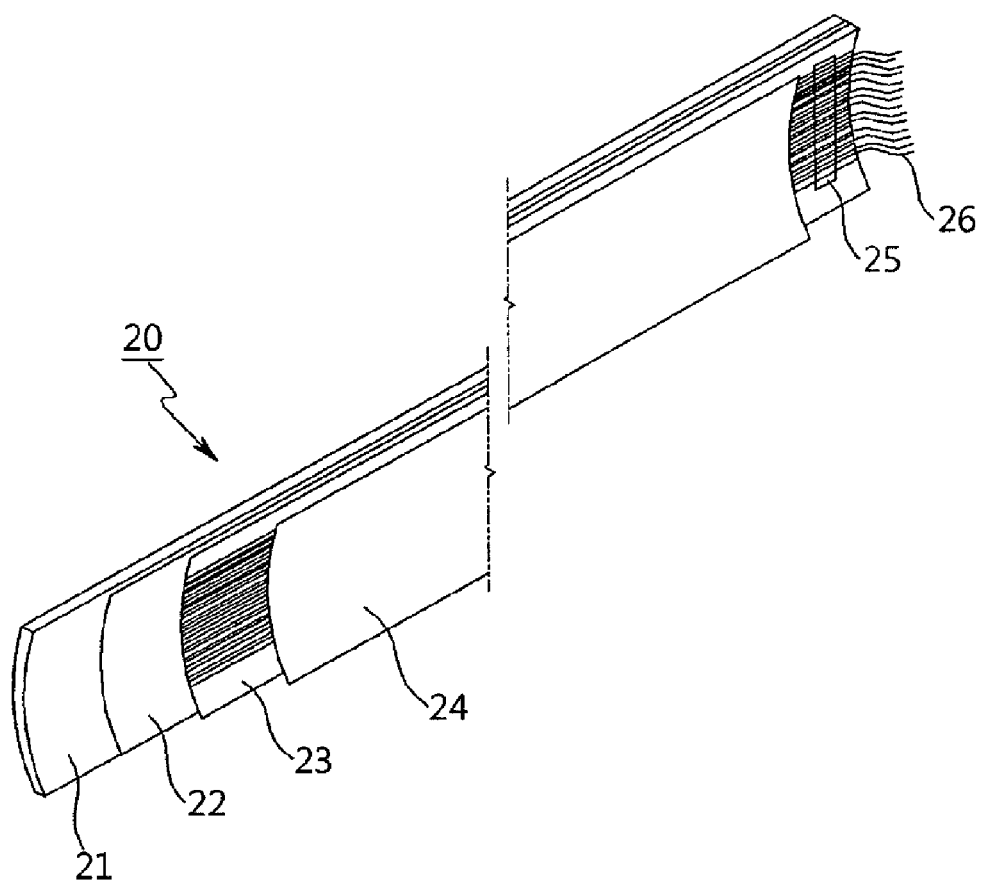
FIG. 3 is a view illustrating an object insertion means according to the present invention.

FIG. 1 is a perspective view illustrating an arc-shaped flexible printed circuit film type endoscope using an imaging device according to the present invention, FIG. 2 is an exploded perspective view depicting the important parts of the arc-shaped flexible printed circuit film type endoscope using the imaging device according to the present invention, and FIG. 3 is a view illustrating an object insertion means according to the present invention. The arc-shaped flexible printed circuit film type endoscope using the imaging device according to the present invention includes an image photographing means 10 and an object insertion means 20. The image photographing means 10 includes a head housing 13 to which an imaging device 11 and an illumination means 12 are mounted, and photographs an image. The object insertion means 20 includes an arc-shaped flexible thin foil 21, an insulating adhesive film 22, a circuit film 23 and an insulating protective film 24 which are layered and inserted into the interior of an object to be inspected. The object insertion means 20 is connected at one end thereof to the image photographing means 10 and connected at the other end to a transmission cable 26 through a connector 25.

The imaging device 11 is a CCD camera or a CMOS sensor. The illumination means 12 comprises LED lamps, and is configured so that lamp supports 12b are inserted into corresponding support insertion grooves 13b of the head housing 13 in such a way that each LED lamp 12a mounted to the corresponding lamp support 12b is inserted into a corresponding lamp insertion hole 13a of the head housing 13, and thereby a terminal contact point formed on the back of each lamp support 12b is in contact with a terminal contact point formed on a side surface of the rear portion of the corresponding support insertion groove 13b.

Further, the head housing 13 includes a plurality of lamp insertion holes 13a which are formed in the upper and lower portions of the front end of the head housing 13. The plurality of support insertion grooves 13b is formed in the head housing 13 to communicate with the lamp insertion holes 13a. A window 13c is formed in the central portion of the front end of the head housing 13. An imaging device insertion hole 13d is formed in the middle portion of the head housing 13 in a longitudinal direction thereof to communicate with the window 13c. A terminal contact point of the imaging device 11 is formed on a side surface on the rear portion of the imaging device insertion hole 13d. A connection surface 13e is provided on the rear end of the head housing 13. Pin holes 13f are formed in an end of the connection surface 13e.

The object insertion means 20 is constructed so that one surface of the circuit film 23 is attached to the arc-shaped flexible thin foil 21 via an insulating adhesive film 22, and the insulating protective film 24 is attached to the other surface of the circuit film 23 using an adhesive.

Further, a circuit means and a transmission means for processing and transmitting an image photographed by the imaging device 11 are formed on the circuit film 23.

In the drawings, reference numeral 11a denotes a lens which is mounted to the CCD camera when the CCD camera is used as the imaging device 11. Reference numerals 14 and 15 denote a locking part and locking pins, respectively, which function to connect and lock the object insertion means 20 to the connection surface 13e of the head housing 13. Reference numeral 25 denotes the connector which connects the circuit line of the circuit film 23 to the transmission cable 26.

Hereinafter, the assembly and use of the arc-shaped flexible printed circuit film type endoscope using the imaging device according to the present invention which is constructed as described above will be described.

First, the LED lamps 12a are inserted into the corresponding lamp insertion holes 13a of the head housing 13, and the lamp supports 12b are inserted into the corresponding support insertion grooves 13b in such a way that the LED lamp terminal contact point formed on the back of each lamp support 12b is in contact with the terminal contact point formed on the side surface of the rear portion of the corresponding support insertion groove 13b. Next, silicone is injected between the support insertion grooves 13b and the corresponding lamp supports 12b so as to secure the LED lamps 12a to the interior of the head housing 13.

Thereafter, the imaging device 11 is inserted into the imaging device insertion hole 13d of the head housing 13 in such a way that the terminal of the imaging device 11 comes into contact with the terminal contact point of the imaging device 11 which is formed on the rear portion of the imaging device insertion hole 13d. Next, the silicone is injected between the imaging device insertion hole 13d and the imaging device 11 so as to secure the imaging device 11 to the interior of the head housing 13.

Subsequently, an end of the object insertion means 20 is connected to the connection surface 13e of the head housing 13, and the locking pins 15 pass through pin holes in the locking part 14 to be inserted into the corresponding pin holes 13f of the head housing 13. Thereby, the assembly of the endoscope is completed.

The endoscope according to the present invention constructed as described above is mounted to a robot which may be used in a small space. For example, the endoscope photographs very narrow gaps between heat transfer tubes which are provided on a secondary side's tube sheet of a steam generator installed in a nuclear power plant, thus inspecting the gaps between the heat transfer tubes.

That is, an image which is photographed by the imaging device 11 secured to the head housing 13 is processed by the circuit means which is provided on the circuit film 23 of the object insertion means 20. Next, the processed image is transmitted by the transmission means through the connector 25 and the transmission cable 26 to an additional display means or a micro-computer. Thereby, by analyzing the transmitted image, the interior of the object can be inspected and displayed.

As described above, the present invention provides an arc-shaped flexible printed circuit film type endoscope using an imaging device, in which a flexible printed circuit film is connected to a head housing accommodating a CCD camera or a CMOS sensor as the imaging device, so that the endoscope can be mounted to a small space such as a robot to easily inspect the interior of a narrow heat transfer tube or gaps between heat transfer tubes, and which utilizes a flexible thin foil having an arc-shaped cross-section, thus ensuring linearity in shape even though the endoscope is very thin, therefore having both linearity and flexibility, and which has a small bending radius, thus being convenient to manipulate the endoscope in a small space, and in which a circuit means or a transmission means for processing or transmitting an image photographed by the imaging device are formed on the flexible printed circuit film, thus realizing a simple structure, therefore achieving high economic efficiency due to reduction in time and costs required to manufacture a product, and increasing the reliability of endoscopy because there is no possibility of failure or malfunction, and increasing the lifespan of the endoscope such that it can be reliably used for a lengthy period of time.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. An arc-shaped flexible printed circuit film type endoscope using an imaging device, comprising:
    image photographing means including a head housing to which an imaging device and an illumination means are mounted, and photographing an image; and
    object insertion means including an arc-shaped flexible thin foil, an insulating adhesive film, a circuit film and an insulating protective film which are layered and inserted into an interior of an object to be inspected, the object insertion means being connected at a first end thereof to the image photographing means and connected at a second end thereof to a transmission cable via a connector.

2. The arc-shaped flexible printed circuit film type endoscope using the imaging device as set forth in claim 1, wherein the imaging device comprises a CCD camera or a CMOS sensor.

3. The arc-shaped flexible printed circuit film type endoscope using the imaging device as set forth in claim 1, wherein the illumination means comprises a LED lamp, and is configured so that a lamp support is inserted into a support insertion groove of the head housing in such a way that the LED lamp mounted to the lamp support is inserted into a lamp insertion hole of the head housing, and a LED terminal contact point formed on a back of the lamp support is in contact with a terminal contact point formed on a side surface of a rear portion of the support insertion groove.

4. The arc-shaped flexible printed circuit film type endoscope using the imaging device as set forth in claim 1, wherein the head housing comprises:
    a plurality of lamp insertion holes formed in upper and lower portions of a front end of the head housing;
    a plurality of support insertion grooves communicating with the lamp insertion holes;
    a window formed in a central portion of the front end of the head housing;
    an imaging device insertion hole formed in a middle portion of the head housing in a longitudinal direction thereof to communicate with the window, with a terminal contact point of the imaging device formed on a side surface on a rear portion of the imaging device insertion hole; and
    a connection surface provided on a rear end of the head housing, with a pin hole formed in an end of the connection surface.

5. The arc-shaped flexible printed circuit film type endoscope using the imaging device as set forth in claim 1, wherein the object insertion means is constructed so that a first surface of the circuit film is attached to the arc-shaped flexible thin foil via an insulating adhesive film, and the insulating protective film is attached to a second surface of the circuit film using an adhesive.

6. The arc-shaped flexible printed circuit film type endoscope using the imaging device as set forth in claim 5, wherein circuit means and transmission means for processing and transmitting an image photographed by the imaging device are formed on the circuit film.

\* \* \* \* \*